(12) United States Patent
Weber

(10) Patent No.: US 7,294,134 B2
(45) Date of Patent: Nov. 13, 2007

(54) SURGICAL INSTRUMENT FOR THE INTRODUCTION OF A MULTI-COMPONENT INTERVERTEBRAL PROSTHESIS

(75) Inventor: Helmut Weber, Emmingen-Liptingen (DE)

(73) Assignee: Weber Instrumente GmbH (DE)

( * ) Notice: Subject to any disclaimer, the term of this patent is extended or adjusted under 35 U.S.C. 154(b) by 69 days.

(21) Appl. No.: 10/900,647

(22) Filed: Jul. 28, 2004

(65) Prior Publication Data

US 2006/0025777 A1 Feb. 2, 2006

(51) Int. Cl.
*A61B 17/58* (2006.01)
(52) U.S. Cl. ...................................... 606/99
(58) Field of Classification Search ............... 606/99, 606/105; 623/17.11–16
See application file for complete search history.

(56) References Cited

U.S. PATENT DOCUMENTS

| 4,997,432 | A | * | 3/1991 | Keller | 606/61 |
| 5,314,477 | A | | 5/1994 | Marnay | |
| 5,716,360 | A | * | 2/1998 | Baldwin et al. | 606/80 |
| 2003/0229358 | A1 | * | 12/2003 | Errico et al. | 606/99 |
| 2004/0117022 | A1 | | 6/2004 | Marnay et al. | |
| 2004/0143331 | A1 | * | 7/2004 | Errico et al. | 623/17.14 |
| 2004/0143332 | A1 | * | 7/2004 | Krueger et al. | 623/17.14 |
| 2004/0220582 | A1 | * | 11/2004 | Keller | 606/99 |
| 2005/0015094 | A1 | * | 1/2005 | Keller | 606/99 |
| 2005/0021042 | A1 | * | 1/2005 | Marnay et al. | 606/99 |
| 2005/0033305 | A1 | * | 2/2005 | Schultz | 606/99 |
| 2005/0119665 | A1 | * | 6/2005 | Keller | 606/99 |
| 2005/0131542 | A1 | * | 6/2005 | Benzel et al. | 623/17.13 |
| 2005/0131543 | A1 | * | 6/2005 | Benzel et al. | 623/17.13 |
| 2005/0143749 | A1 | * | 6/2005 | Zalenski et al. | 606/99 |

FOREIGN PATENT DOCUMENTS

| DE | 299 16 078 | 11/1999 |
| DE | 102 25 703 | 5/2003 |
| DE | 203 10 433 | 9/2003 |
| EP | 1 222 903 | 7/2002 |

* cited by examiner

*Primary Examiner*—Eduardo C. Robert
*Assistant Examiner*—Annette Reimers
(74) *Attorney, Agent, or Firm*—Akerman Senterfitt; Stephan A. Pendorf; Peter A. Chiabotti

(57) ABSTRACT

A surgical instrument for the introduction of an intervertebral prosthesis (10) including at least three components, namely, two prosthesis plates (14, 16) and a prosthesis core (12). The surgical instrument can include a U-shaped holder (30) at the distal end of a gripping element (20) into which the intervertebral prosthesis (10) with all the components can be detachably introduced whereby the individual components are aligned with respect to one another in a fixed manner.

20 Claims, 6 Drawing Sheets

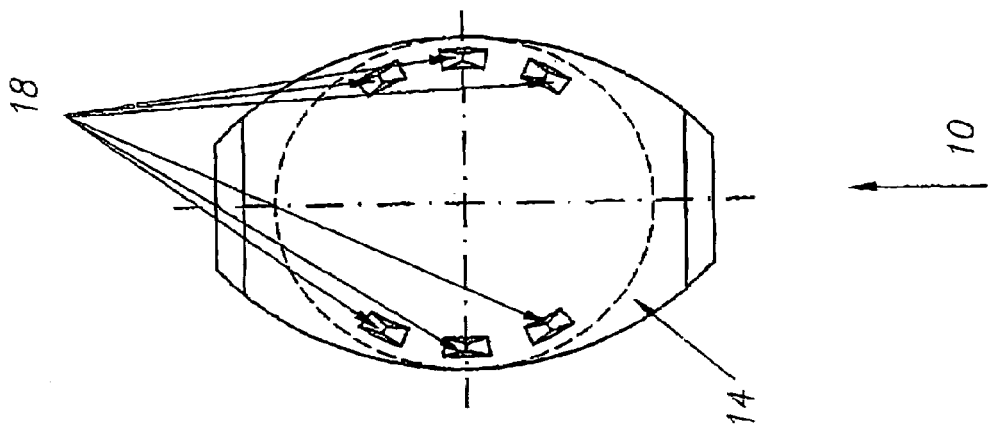
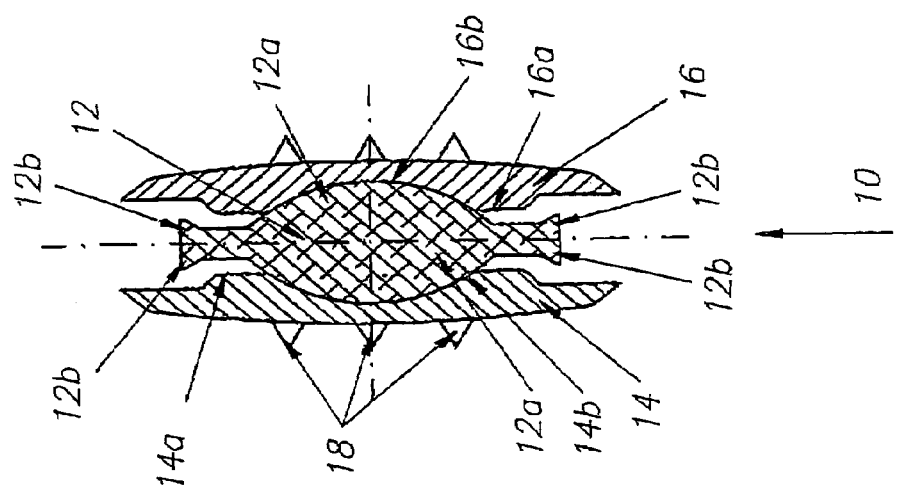
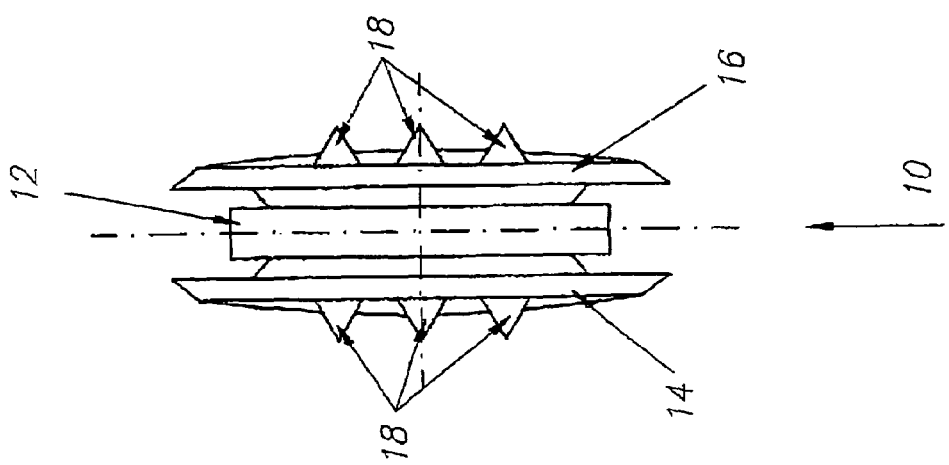

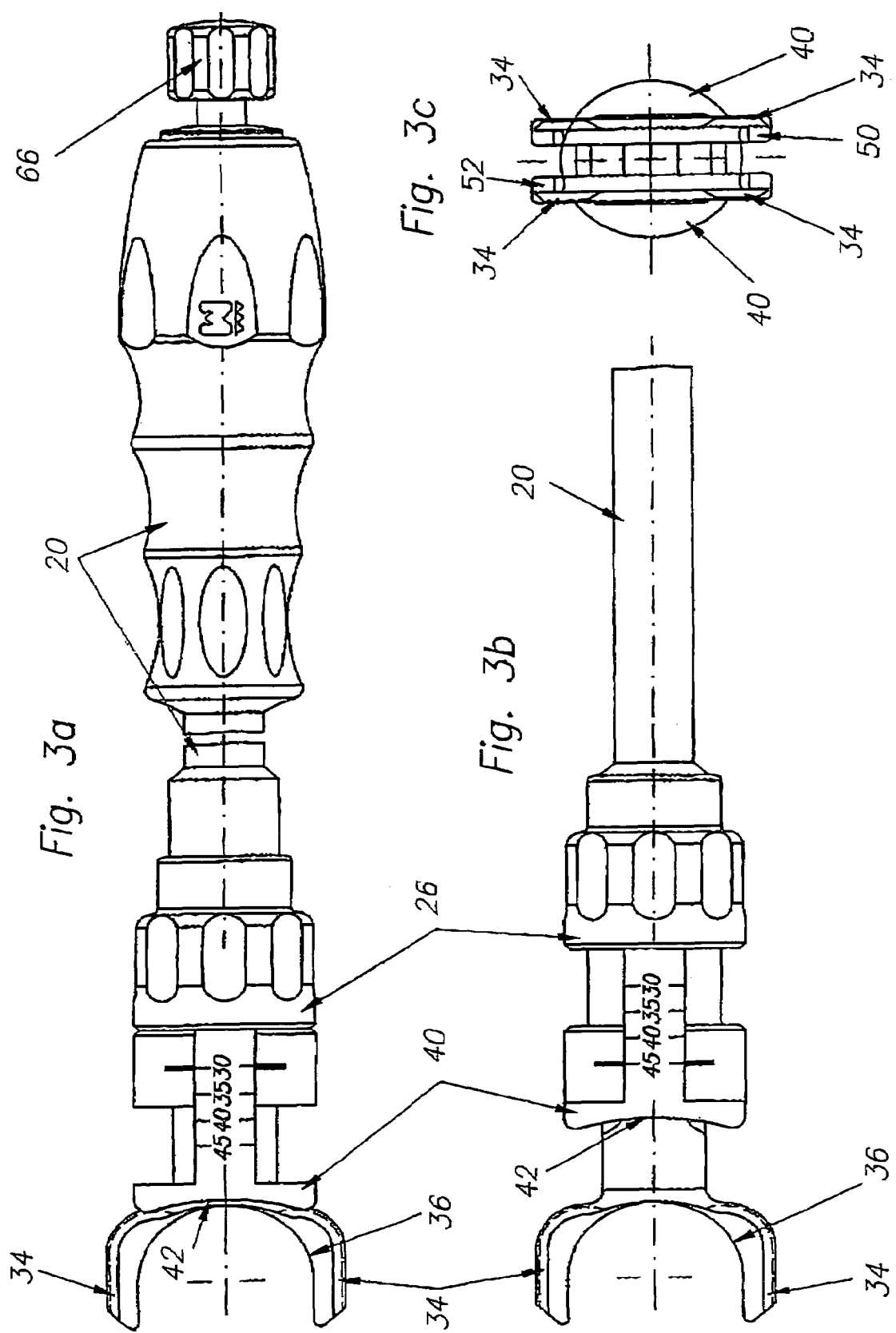

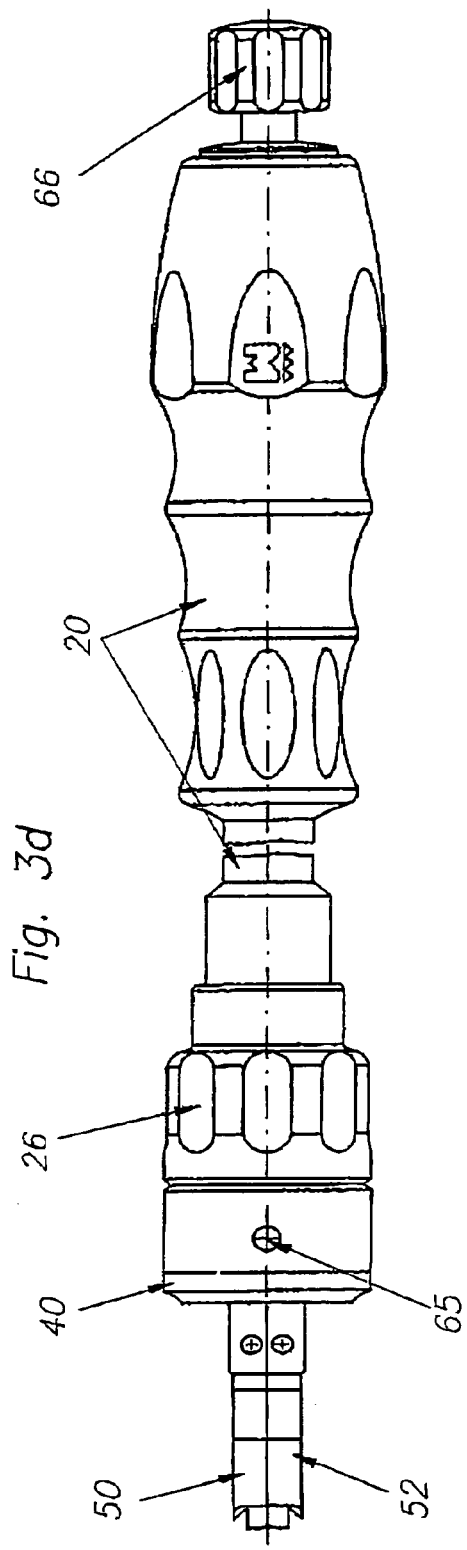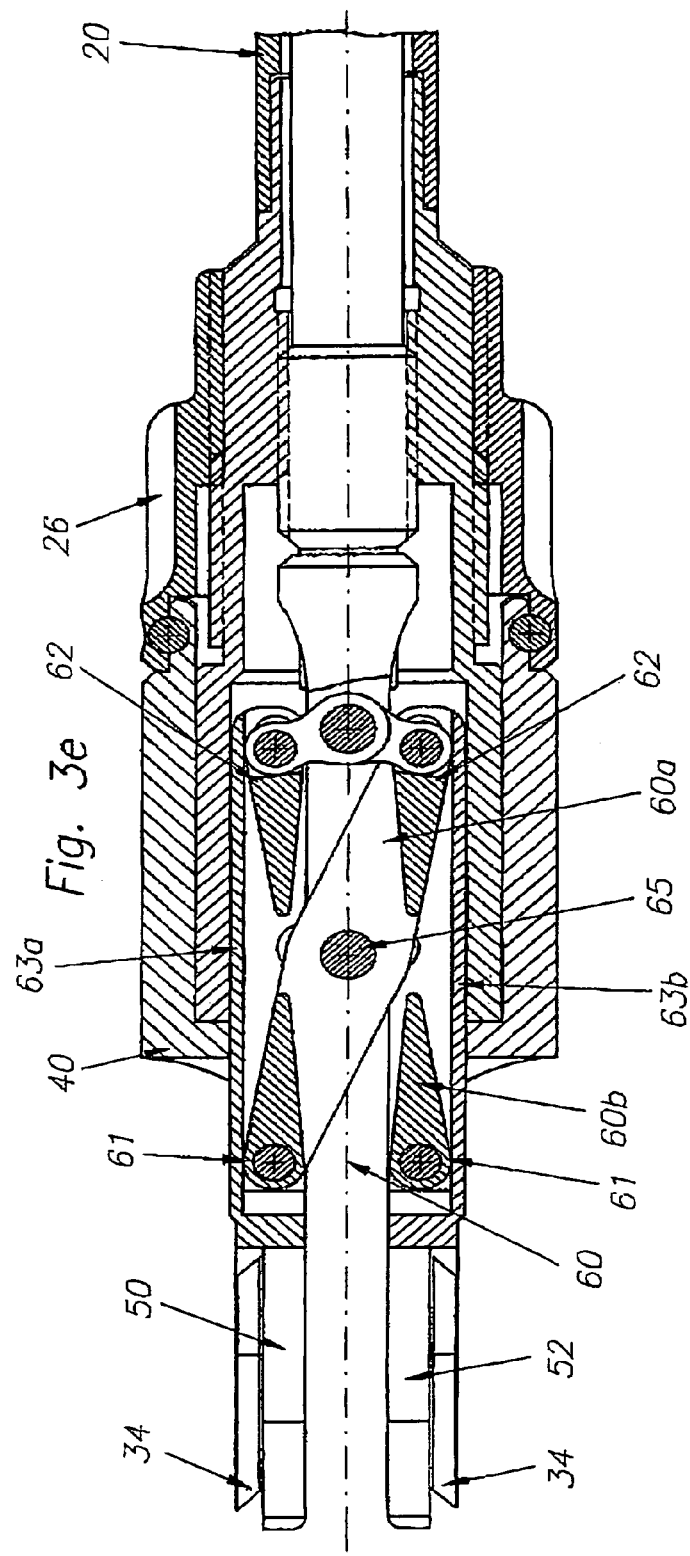
Fig. 3d
Fig. 3e

SURGICAL INSTRUMENT FOR THE INTRODUCTION OF A MULTI-COMPONENT INTERVERTEBRAL PROSTHESIS

FIELD OF THE INVENTION

The invention concerns a surgical instrument for the introduction of a multi-component intervertebral prosthesis.

BACKGROUND OF THE INVENTION

Various instruments are known for the introduction of multi-component, especially three-component, intervertebral prostheses, which consist of two prosthesis plates, each of which is joined to a vertebral body, and a prosthesis core arranged between them.

A surgical instrument for the introduction of intervertebral prostheses is known from EP 0 333 990 A2 which consists of expanding tongs that have a holder for a prosthesis plate on the front end on each jaw. The two prosthesis plates can be first made to come very close to the expanding tongs in order to introduce them into the space between the neighboring vertebrae. Then the expanding tongs are spread out in order to be able to introduce the prosthesis core between the prosthesis plates.

DE 299 19 078 U1 discloses a surgical instrument for the introduction of intervertebral implants, which has two guide tracks that are supported pivotably at the back end, and each of which has a holding device for a prosthesis plate on their free end. A longitudinal guide for the prosthesis core is arranged between the two arms. First the two prosthesis plates are introduced into the intervertebral space in the closed position, and then the two prosthesis holders are spread apart whereby, at the same time, the prosthesis core is pushed to the distal end of the instrument until it reaches the desired end position between the prosthesis plates.

DE 102 25 703 A1 discloses an instrument for the introduction of an intervertebral prosthesis which has two prosthesis holders for a pair of prosthesis plates, the holders being joined through a parallel guide and can be separated from one another, where all parts joining the two prosthesis holders are arranged outside a middle entry opening running in the longitudinal direction of the instrument, the width of which corresponds at least to the transverse measurements of the prosthesis core to be introduced between the prosthesis plates and to the prosthesis core holder provided for this. Again, first the two prosthesis plates are introduced with the aid of the instrument and then the prosthesis plates are spread apart and the prosthesis core is introduced.

On the surfaces facing each other, the prosthesis plates have concave recesses between which the prosthesis core is set, which has similarly-formed convex protrusions. The bowed surfaces of the prosthesis plates and the prosthesis core can slide on one another within certain limits and thus permit tilting and rotation of the upper prosthesis plate with respect to the lower one, as a result of which the mobility of the spinal column section in which the intervertebral prosthesis is introduced, is ensured.

Therefore, in order to be able to introduce the prosthesis core between the two prosthesis plates, the prosthesis plates have to be spread apart relatively far so that the convex protrusions of the prosthesis core are able to slide in over the edge of the concave recesses in the prosthesis plates. Such a large spreading of the intervertebral space should, however, be avoided as much as possible in order to be able to exclude damage to the spinal column and to the vertebrae. Furthermore, the prosthesis core is usually introduced in such a way that the intervertebral space is not completely spread apart, in order to be able to introduce the prosthesis core without any expenditure of force, but that the prosthesis core is driven into a smaller intermediate space between the prosthesis plates, in which case the intervertebral space is spread especially widely only in the instant in which the convex protrusions of the prosthesis core slide over the edge of the concave recesses in the prosthesis plates. However, in this case, the prosthesis core is exposed to large loads since the force that spreads the intervertebral space acts on it so that the surface of the prosthesis core can become damaged.

SUMMARY OF THE INVENTION

Therefore, the task of the invention is to provide a surgical instrument for the insertion of intervertebral prostheses, an instrument which is easier to handle and at the same time permits as protective insertion of the intervertebral prosthesis as possible, protecting both the patient as well as the prosthesis core.

The task according to the invention is solved by a surgical instrument according to Patent claim 1.

Advantageous embodiments and further developments of the invention are given in the subclaims.

The surgical instrument for the introduction of an at least three-part intervertebral prosthesis according to the invention has a U-shaped holder at the distal end of a gripping element into which the intervertebral prosthesis, consisting of two prosthesis plates and a prosthesis core, can be inserted removably with all the components, where the individual components are lined up to one another in a fixed manner.

With the surgical instrument according to the invention, the intervertebral prosthesis is introduced together with all the components into the intervertebral space, which is held separated with the aid of another instrument and is kept open. The advantage is first of all that the prosthesis core is already introduced between the two prosthesis plates so that subsequent introduction of the prosthesis core between the prosthesis plates is not needed and thus increased spreading of the intervertebral space is avoided. Another advantage lies in the fact that all components of the intervertebral prosthesis are kept aligned with respect to one another so that it is ensured that, even when inserted into the intervertebral space, no tilting or twisting of the prosthesis plates against one another is possible. The U-shaped holder of the instrument according to the invention ensures that the intervertebral prosthesis is safely introduced between the vertebrae from the access side and then can be removed again, without twisting or unnecessarily moving the intervertebral prosthesis.

Preferably the U-shaped holder has clamping elements for the intervertebral prosthesis. In this case, the intervertebral prosthesis can be introduced into the intervertebral space with the surgical instrument, whereupon the spreading of the intervertebral space is eliminated. The teeth arranged outside the prosthesis plates engage into the neighboring vertebrae. This engagement is sufficient to overcome the clamping of the intervertebral prosthesis in the U-shaped holder when the surgical instrument is removed so that no additional mechanism is needed for separating the prosthesis.

In an advantageous further development of the invention, the clamping elements are designed as two leaf springs running on the inside along the leg of the U-shaped holder. The leaf springs are especially simple to manufacture and also can be molded in one piece against the U-shaped holder.

Preferably the clamping elements hold the prosthesis core. Especially in combination with an aligning device for the prosthesis plates, this is sufficient to safely fix the intervertebral prosthesis.

In an advantageous further development of the invention, the inner contour of the U-shaped holder is designed corresponding to the outside contour of the prosthesis core. In this way, it is ensured that the prosthesis core is held especially securely.

Preferably, the inner contour of the U-shaped holder is designed as a circular arc of about 200°. The inner contour of the U-shaped holder thus surrounds slightly more than half of the circular prosthesis core, and has an opening between the legs of the U-shaped holder, which is smaller than the diameter of the prosthesis core. In this way, clamping of the prosthesis core is achieved reliably.

In an advantageous further development of the invention, two guide tracks are formed in the plane of each of the U-shaped holders on the inside of the leg of the U-shaped holder for holding the prosthesis plates. The prosthesis plates can thus be inserted in the guide tracks as an individual element without resistance. Holding the intervertebral prosthesis is achieved by the fact that the convex protrusions of the prosthesis core engage in the concave recesses of the prosthesis plates and thus the prosthesis plates are also securely held in the U-shaped holder, although the prosthesis plates are not clamped. Furthermore, the guide tracks for holding the prosthesis plates provide alignment of the prosthesis plates with respect to the prosthesis core and to one another. For this purpose, preferably the guide tracks for holding the prosthesis plates are arranged parallel to one another. Preferably for this purpose, furthermore, the guide tracks are arranged on both sides of the leaf springs running along the legs of the U-shaped holder.

Preferably, connected to the U-shaped holder a stop is present which can be moved along the axis of the gripping elements. This stop serves to define when the intervertebral prosthesis has reached the desired end position as is introduced into the intervertebral space. As a rule, the intervertebral space, which is formed during surgery after removal of the defective disk, is probed with a control prosthesis in order to determine the preferred size of the intervertebral prosthesis and accurate positioning of it. In order to see, correspondingly, on the surgical instrument according to the invention for introduction of the intervertebral prosthesis, how far the instrument with the intervertebral prosthesis must be introduced into the intervertebral space in order to position the intervertebral prosthesis optimally, the value determined with the control prosthesis can be adjusted at the moveable stop. As soon as the stop encounters the outside contour of the neighboring vertebra, the optimum position for the intervertebral prosthesis is reached.

For this purpose, the stop is arranged preferably perpendicularly to the plane of the U-shaped holder in order to provide a defined stop point.

Preferably, the stop meets the gripping element perpendicularly and projects on both sides of the gripping element. In this way, it ensures that the operator can see the stop independently of whether the surgical instrument is rotated by 180° around the longitudinal axis or not.

Preferably, a thread engages in the stop, this thread runs along the axis of the gripping element and can be adjusted with the aid of a screw element. This makes it possible to move the stop simply along the longitudinal axis of the gripping element and also ensures that when the stop reaches the vertebral body, the stop cannot be displaced along an axis parallel to the longitudinal axis of the gripping element by a pressure on the stop.

In an advantageous further development of the invention, the U-shaped holder is made of two parts, where the two holding elements of the U-shaped holder are joined through a parallel guide and can be spread apart and then closed again. Such a design of the U-shaped holder makes it possible to be able to hold intervertebral prostheses of different heights with the same instrument. Thus, for different intervertebral prostheses which are needed to fit the different shapes of the vertebrae of different persons, the surgical instruments needed for the different heights of the intervertebral prostheses can be the same. Therefore, different surgical instruments are not needed for the different heights of intervertebral prostheses.

Preferably the two elements of the U-shaped holder each have on the inside of the legs facing away from one another a guide track for holding the prosthesis plate. Since as a rule the height of the intervertebral prosthesis varies according to the height of the prosthesis core, it is ensured that the intermediate space between the clamped prosthesis plates in the U-shaped holder can be varied.

BRIEF DESCRIPTION OF THE DRAWINGS

The invention will be explained in detail with the aid of the following figures. The following are shown.

DETAILED DESCRIPTION OF THE INVENTION

Figure 1D:
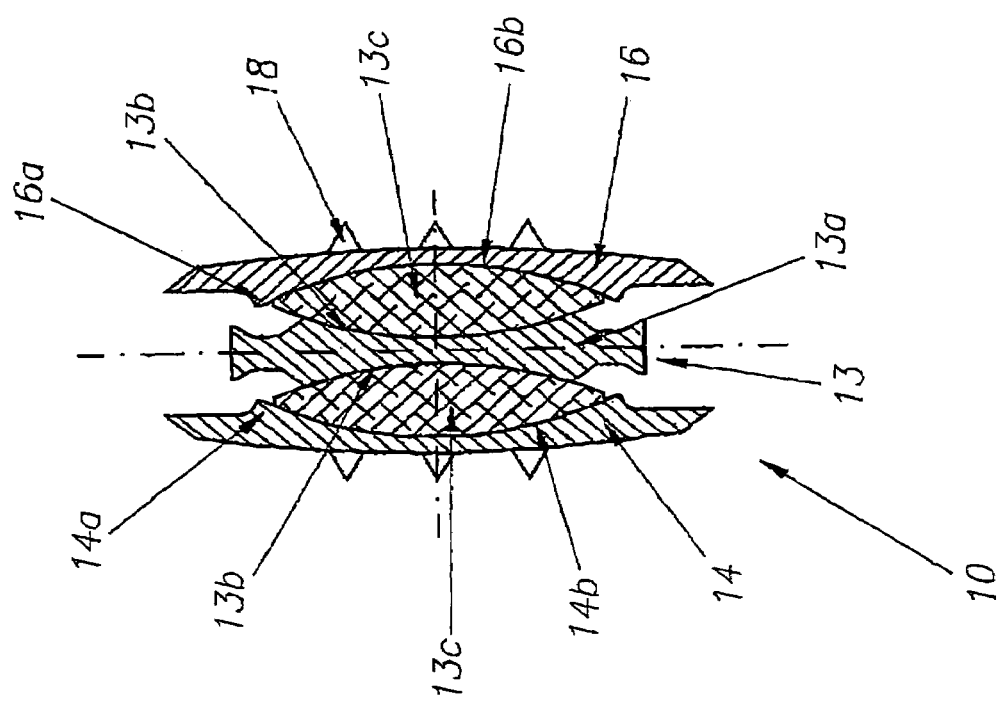
FIG. 1a is a side view of a three-part intervertebral prosthesis.
FIG. 1b is an axial section through the intervertebral prosthesis according to FIG. 1a, FIG. 1c is a top view onto the intervertebral prosthesis according to FIG. 1a, FIG. 1d is an axial section through a second practical example of an intervertebral prosthesis.

FIGS. 1a, 1b and 1c show an intervertebral prosthesis 10 consisting of a prosthesis core 12 and two prosthesis plates 14, 16, which enclose the prosthesis core 12. The prosthesis core 12 consists of a circular disk which has on both sides an axially arranged spherical segment 12a and a ring land 12b protruding axially and running at the outer edge.

The two prosthesis plates 14 and 16 are designed identically and consist of an ellipsoidal disk, the main vertices of which are flattened and where a circular torus 14a, 16a is arranged on one side of the disk, and this torus has a recess 14b, 16b having the shape of a spherical shell. In the composed state of the intervertebral prosthesis 10, the spherical segments 12a of the prosthesis core 12 lie in the recesses having the shape of a spherical shell 14b, 16b of the prosthesis plates 14, 16. On the side of the prosthesis plates 14, 16 away from the prosthesis core 12 there are several teeth 18 arranged, in this case six, which anchor the prosthesis plates 14, 16 in the neighboring vertebra. In the present practical example, the sides of the prosthesis plates 14, 16 away from the prosthesis core 10 are designed to be flat. In order to be able to adapt the prosthesis plates 14, 16 to the slopes of the neighboring vertebrae, the side of the prosthesis plates 14, 16 facing away from the prosthesis core 10 can be inclined to the plane of prosthesis plate 14, 16.

FIG. 1d shows an axial section through another embodiment of the intervertebral prosthesis 10, consisting of the two prosthesis plates 14, 16 and a three-part prosthesis core 13. Here the prosthesis core 13 is designed so that a recess 13b having the shape of a spherical shell is formed in a disk-shaped middle element 13a on both sides and a sliding element 13c is set in each one of these, consisting of two spherical segments of the same diameter. The spherical segment of the sliding element 13c facing the middle element 13a is thus arranged so that it can slide in the recesses 13b, having the shape of a spherical shell, of the middle element 13a, while the spherical segment of the sliding element 13c facing away from middle element 13a lies in the spherical-shell-shaped recesses 14b, 16b of prosthesis plate 14, 16 and is arranged in these so that it can slide. A prosthesis core 13 made of several parts make additional degrees of freedom of the movement of the two prosthesis plates 14, 16 with respect to one another possible, as a result of which the mobility of the spinal column section into which the intervertebral prosthesis 10 was implanted is further enhanced.

Figures 2A, 2B:
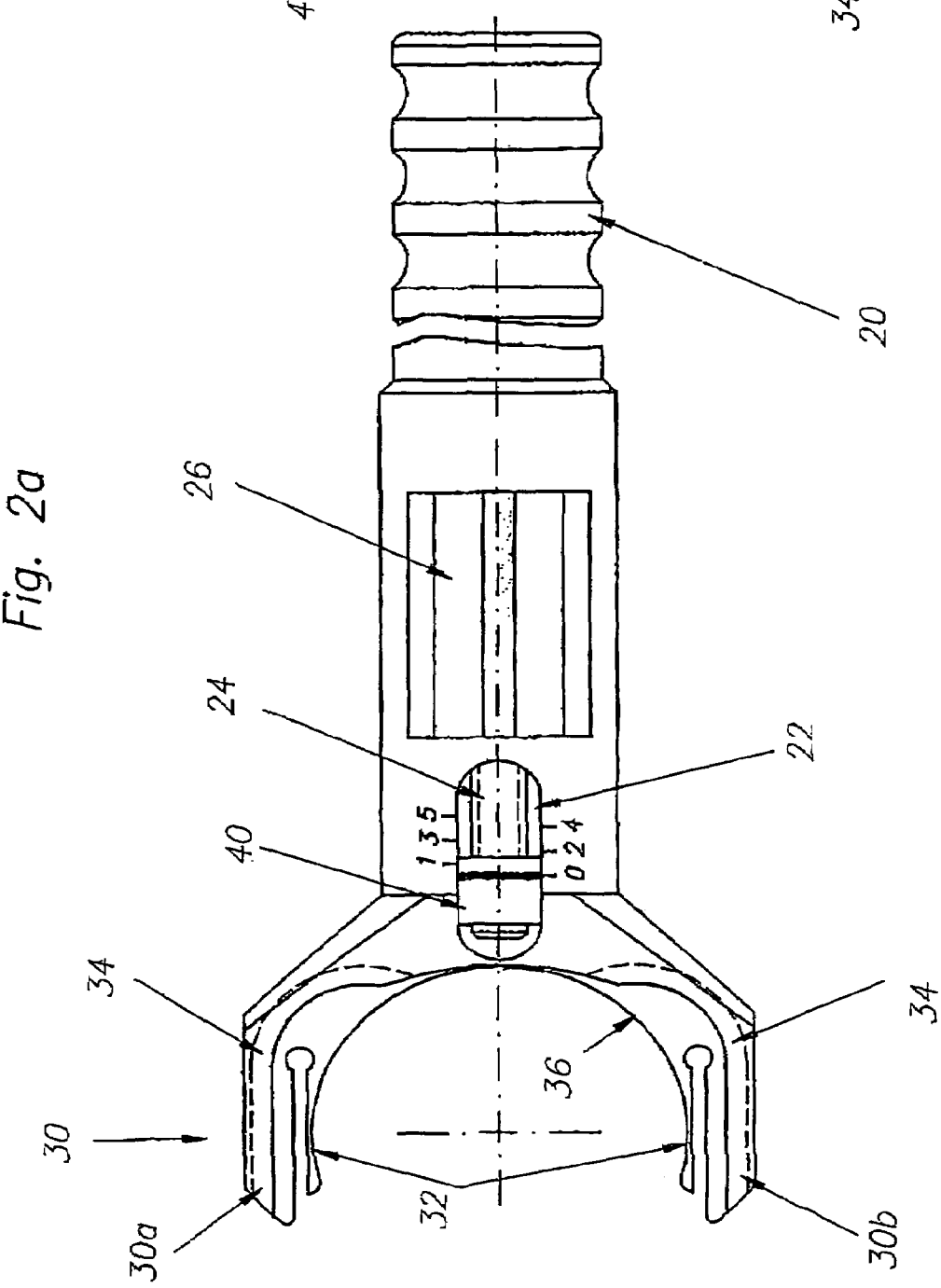
FIG. 2a is a top view on a first practical example of a surgical instrument for introducing an intervertebral prosthesis.
FIG. 2b is a view axially from the top onto the practical example according to FIG. 1d.

FIGS. 2a and 2b show two views of a first practical example of a surgical instrument for introducing a multi-component intervertebral prosthesis 10, consisting of a gripping element 20 which has a U-shaped holder 30 on its distal end. The axis of the gripping element 20 lies in the plane fixed by the U-shaped holder 30. The U-shaped holder 30 has two legs 30a, 30b and a leaf spring 32 is arranged on the inside of each of these parallel to legs 30a, 30b. The inner contour 36 of the U-shaped holder 30, formed essentially by the two leaf springs 32, is designed as a circular arc of about 200°. In this way, the opening between the distal ends of the leaf springs 32 is slightly smaller than the maximum diameter of the circular arc. Thus, when the disk-shaped prosthesis core 12 with its circular outer contour is introduced between the two leaf springs 32, the leaf springs 32 first slightly relax and lie against the outer contour of prosthesis core 12. In this way, secure clamping of the prosthesis core 12 between the leaf springs 32 is ensured.

On the inside of legs 30a, 30b of the U-shaped holder 30, on both sides, along the leaf springs 32, guide tracks 34 are made to hold prosthesis plates 14, 16. Here, the distances between the two legs 30a, 30b corresponds to the length of the main axis of the essentially ellipsoidal disk of the prosthesis plates 14, 16. The guide tracks 34 run on each leg 30a, 30b parallel to one another, in order to provide a parallel alignment of the prosthesis plates 14, 16. The distance between the guide tracks 34 on each of legs 30a, 30b corresponds to the distance of the prosthesis plates 14, 16 in the assembled state of the intervertebral prosthesis 10. When the intervertebral prosthesis 10 is placed into the U-shaped holder 30, only the prosthesis core 12 is held by clamping. In principle, the prosthesis plates 14, 16 can move in the guide tracks without any resistance. However, due to the insertion of the spherical segments 12a of the prosthesis core 12 into the spherical-shell-shaped recesses 14b, 16b and the exact parallel alignment of the prosthesis plates 14, 16 to one another, they are also held safely in the U-shaped holder 30.

Following the U-shaped holder 30, in gripping element 20, a stop 40 is arranged which can be moved along the axis of gripping element 20. The stop 40 goes through the gripping element in a radial opening 22 and protrudes out of the gripping element 20 on both sides. The stop is perpendicular to the axis of the gripping element and perpendicular to the plane of the U-shaped holder 30. A thread 24 goes through stop 40 along the axis of gripping element 20 and this thread can be rotated with the aid of a screwing element 26. Since stop 40 cannot be rotated in the radial opening 22, stop 40 moves along the axis of gripping element 20 when the screwing element 26 and thus thread 24 are turned. When stop 40 is moved as far as possible in the direction of the distal end of the surgical instrument, the intervertebral prosthesis 10 is not introduced as far into the intervertebral space as when the stop 40 is removed as far as possible away from the distal end of the surgical instrument, and thus, when introducing the instrument into the intervertebral space, it will meet the neighboring vertebra later.

FIG. 2b shows an axial top view onto the first practical example in which especially the parallel guide tracks 34 intended for holding the prosthesis plates 14, 16 can be seen clearly. Furthermore, FIG. 2b shows the intermediate space between the leaf springs 32 and the guide tracks 34 into which the prosthesis core 12 can be inserted and in which it is fixed by the leaf springs 32 removably.

Figure 3F:
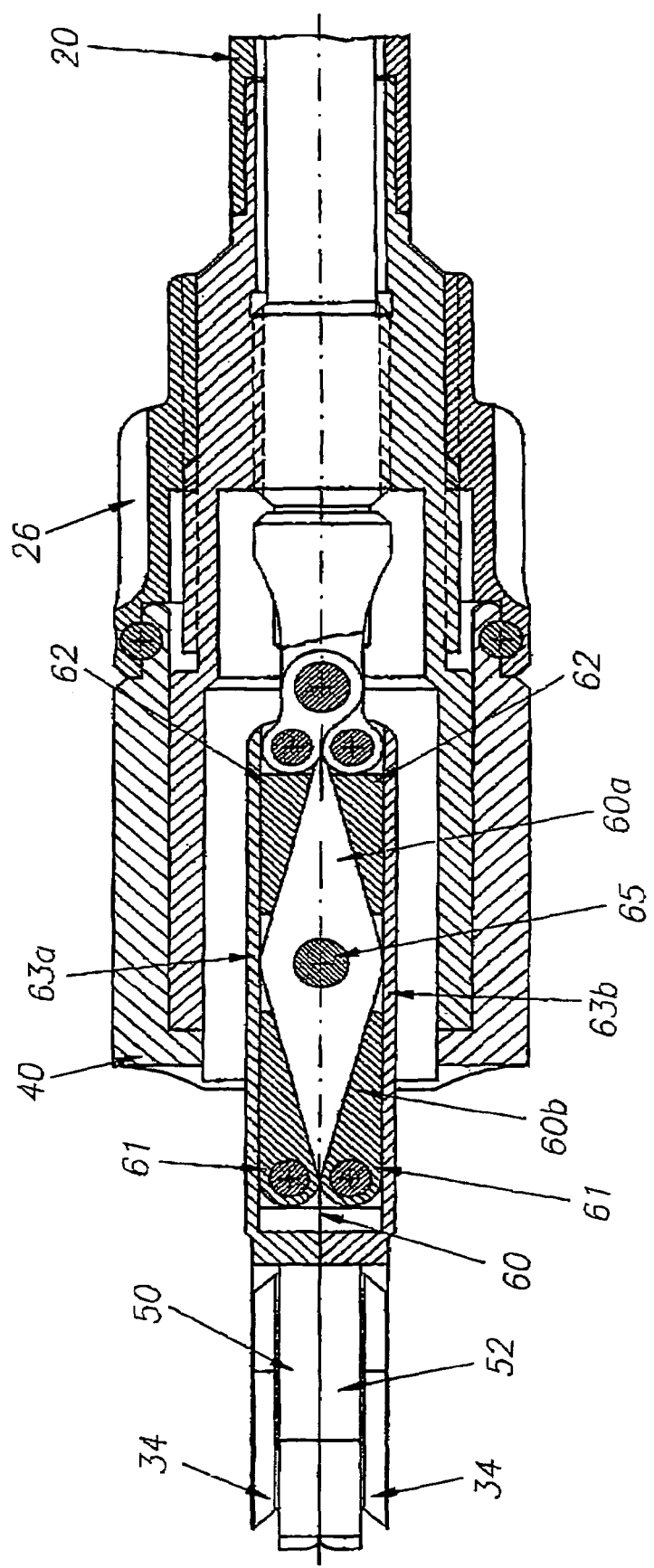
FIG. 3a is a top view onto a second practical example of a surgical instrument for introducing an intervertebral prosthesis.
FIG. 3b is a top view onto the practical example according to FIG. 3a with the stop set back.
FIG. 3c is a view axially from the top onto the practical example according to FIG. 3a, FIG. 3d is a side view of the practical example according to FIG. 3a, FIG. 3f is an axial section through the practical example according to FIG. 3a in the closed state.
FIG. 3e is an axial section through the practical example according to FIG. 3a in the spread-apart state.

FIGS. 3a to 3f show a second practical example of a surgical instrument for the introduction of the intervertebral prosthesis 10. The second practical example of the surgical instrument according to the invention has a U-shaped holder consisting of two holding elements 50, 52. Each element 50, 52 is essentially identical to the U-shaped holder 30, but only one guide track 34 is arranged in each of holding elements 50, 52. The two holding elements 50, 52 are arranged at the distal end of gripping element 20 in such a way that the sides of the holding elements 50, 52, which have the guide tracks 34, lie on the sides away from one another, while the sides of the holding elements 50, 52 which have no guide tracks are facing one another. When the two holding elements 50, 52 lie directly on one another, as shown in FIG. 3d, essentially the U-shaped holder 30 is obtained, which was symmetrically separated by the plane placed through the U.

The two holding elements 50, 52 are connected through a parallel guide 60 and can be spread apart. FIGS. 3e and 3f each show an axial section through the second practical example of the instrument according to the invention with two different positions of the parallel guide 60.

In the known manner, the parallel guide 60 is designed as a pair of scissors with two scissor members 60a, 60b, which are connected to one another so that they can be rotated against one another around their axis of symmetry through an axis 65. The holding elements 50, 52 are arranged on the free end 61 of scissor members 60a, 60b, these free ends lying on the side of axis 65 facing the distal end of the instrument. The free ends 62 of scissor member 60a, 60b lying on the other side of the axis are engaged with a device designed in the known manner, which can move these free ends 62 towards and away from each other. This device can be operated with the aid of a knob 66 arranged at the proximal end of the instrument. The arrangement of the knob 66 at the proximal end of the instrument is advantageous because in this way it is outside the surgery area and thus can be operated easily even when the distal end of the instrument is introduced into the surgery area.

In addition, the free end 61 of the scissor member 60a, 6b is connected to the free end 62 of the other scissor member 60b, 60a through a connecting element 63a, 63b; the holding elements 50, 52 are arranged in the extension of these to the distal end of the instrument, beyond the free ends 61 of scissor member 60a, 60b. When the free ends 62 are moved away from one another, the holding elements 50, 52, which are rotatably supported at the opposite free ends 61 of the scissor members 60a, 60b, are moved away parallel from one another. With such design of the U-shaped holder 30, it becomes possible to introduce intervertebral prostheses 10 of different thicknesses into the intervertebral space with the same instrument.

Thus, having a number of surgical instruments for intervertebral prostheses 10 with different heights becomes unnecessary.

In this embodiment of the instrument, no clamping elements are needed which run parallel to the legs of the U-shaped holder and clamp the prosthesis core along its outside contour. The intervertebral prosthesis is held sufficiently by the fact that the two prosthesis plates 14, 16 are inserted in the guide tracks 34, each in a holding element 50, 52, placing the prosthesis core 12 between them and by bringing the holding elements 50, 52 together, thus providing a clamping action.

FIGS. 3a and 3b show the second practical example in a top view with two different positions of stop 40. The second practical example differs from the first practical example also in the design of stop 40, since the mechanism for displacing the stop 40 is arranged not inside the gripping element 20, but outside the gripping element 20, since the mechanism of the parallel guide 60 is arranged within the gripping element 20.

The stop 40 of the second practical example has a contact contour 42 which corresponds to the ellipsoidal arc around a conjugate vertex of the essentially ellipsoidal prosthesis plates 14, 16. If the stop 40 is moved as far as possible in the direction of the distal end of the surgical instrument, as shown in FIG. 2a, the contact contour 42 lies on the outside contour of prosthesis plates 14, 16. If the surgical instrument with the stop 40 adjusted in this way is introduced into the intervertebral space, the contact contour 42 contacts the intervertebra[sic] as soon as the outside contour of the prosthesis plates 14, 16 coincides with the outside surface of the vertebra.

In addition, stop 40 has a marking which can be brought into coincidence with a marking arranged in a fixed manner on gripping element 20. The marking gives the distance from the contact contour 42 to the conjugate vertex of prosthesis plates 14, 16, which forms the distal end of the surgical instrument. Here the distance is 30 mm.

FIG. 3b shows the stop 40 which is moved back as far as possible from the distal end of the surgical instrument, where the marking shows a clearly larger value, namely 45 mm.

FIG. 3c is a view axially from the top onto the second practical example, in which especially the parallel guide tracks 34 for holding the prosthesis plates 14, 16 can be seen clearly. The prosthesis core 12 is positioned in the intermediate space between the guide tracks 34 and held in a fixed manner by bringing together the two holding elements 50, 52.

In a surgical procedure, the surgical instrument according to the invention is used as follows: after the access to the spinal column is made and the intervertebral space is freed from the diseased disk and is cleaned out, first the size of the intervertebral space is probed with a control prosthesis. Here, the size of the intervertebral prosthesis to be used, that is, the length of the main axis of the essential ellipsoidal prosthesis plates 14, 16 and the thickness of the intervertebral prosthesis 10, that is, especially the thickness of the prosthesis core 12, are determined. Furthermore, the slope of the vertebral surfaces to one another is determined. This will show if prosthesis plates with a plane or an inclined back surface will be used.

Using the control prosthesis, it is also determined how far the intervertebral prosthesis 10 has to be introduced into the intervertebral space. The distance between the outside contour of the vertebra and the desired position of the outside contour of the intervertebral prosthesis 10 is adjusted correspondingly at stop 40.

Then the intervertebral prosthesis 10 is composed from the selected components, namely the desired prosthesis core 12 and the optimized prosthesis plates 14, 16 and is clamped into the third practical example of the surgical instrument according to the invention according to FIGS. 3a and 3b. The prosthesis core 12 is then held by the leaf springs 32, while the prosthesis plates 14, 16 are placed in the guide tracks 34 and are held by the cooperation of the spherical segments 12a of the prosthesis core 12 and the spherical shell-shaped recesses 14b, 16b of prosthesis plates 14, 16. In order to be able to insert the intervertebral prosthesis 10, the intervertebral space must be made wider with another spreading instrument in such a way that the intervertebral prosthesis 10 including the protruding teeth 18 can be introduced into the intervertebral space. Here the spreading instrument is designed so that the surgical instrument for inserting intervertebral prostheses according to the invention can be introduced into the intervertebral space without any problems, the valves [sic, "Valven"]of the spreading instrument not causing any disturbance.

The surgical instrument with the inserted intervertebral prosthesis 10 is now introduced into the intervertebral space until stop 40 contacts the vertebra. The spreading elements are now lowered until the vertebra comes into contact with teeth 18. Then the surgical instrument can be removed without any danger without changing the position of the intervertebral prosthesis 10 since this is held at the vertebrae through teeth 18.

The advantage of this surgical method lies in the fact that a smaller spreading of the intervertebral space is needed since the introduction of the prosthesis core 12 between the prosthesis plates 14, 16, where the spherical segments 12a have to be pressed over the toruses 14a, 16a in the spherical-shell-shaped recesses 14b, 16b, is omitted. Furthermore, exact positioning of the prosthesis plates 14, 16 and of the prosthesis core 12 to one another is provided automatically. Especially, damage to the surface of the prosthesis core 12 is avoided, since the prosthesis core 12 is introduced simultaneously with prosthesis plates 14, 16 into the intervertebral space and not subsequently into the intermediate space between the two prosthesis plates 14, 16.

REFERENCE LIST

10 Intervertebral prosthesis
12 Prosthesis core
12a Spherical segment
12b Ring land
13 Prosthesis core
13a Middle element
13b Spherical-shell-shaped recess
13c Sliding element
14 Prosthesis plate
14a Torus
14b Spherical-shell-shaped recess
16 Prosthesis plate
16a Torus
16b Spherical-shell-shaped recess
18 Teeth
20 Gripping element
22 Radial opening
24 Thread
26 Screwing element
30 U-shaped holder
30a Leg
30b Leg
32 Leaf spring
34 Guide tracks
36 Inside contour
40 Stop
42 Contact contour
50 Holding element
52 Holding element
60 Parallel guide
60a Scissor member
60b Scissor member
61 Free end
62 Free end
63a Connecting element
63b Connecting element
65 Axis
66 Knob

What is claimed is:

1. A surgical instrument for introduction of an intervertebral prosthesis (10), having at least two prosthesis plates (14, 16) and a prosthesis core (12), comprising:
 a gripping element (20);
 a U-shaped intervertebral prosthesis (10) holder (30), the U-shaped intervertebral prosthesis (10) holder (30) located at the distal end of the gripping element (20),
 a vertebrae stop (40) arranged on the gripping element (20) and movable along a lengthwise axis of the gripping element (20);
 wherein the U-shaped holder (30) defines a plane extending along the lengthwise axis of the gripping element (20) that divides the gripping element (20) into a first portion located above the plane and a second portion located below the plane;
 wherein the vertebrae stop (40) extends from above the first portion of the gripping element (20) to below the second portion of the gripping element (20).

2. The surgical instrument according to claim 1, wherein the U-shaped holder (30) has clamping elements for the intervertebral prosthesis (10).

3. The surgical instrument according to claim 2, wherein the clamping elements are designed as two leaf springs (32) running on the inside along the legs (30a, 30b) of the U-shaped holder (30).

4. The surgical instrument according to claim 2, wherein the clamping elements hold the prosthesis core (12).

5. The surgical instrument according to claim 1, wherein the inside contour (36) of the U-shaped holder (30) corresponds to the outside contour of the prosthesis core (12).

6. The surgical instrument according to claim 5, wherein the inside contour (36) of the U-shaped holder (30) is a circular arc of about 2000°.

7. The surgical instrument according to claim 1, wherein two guide tracks (34) are formed in the plane of the U-shaped holder (30) on the inside of each leg (30a, 30b) of the U-shaped holder (30) to hold the prosthesis plates (14, 16).

8. The surgical instrument according to claim 7, wherein the guide tracks (34) run parallel to one another.

9. The surgical instrument according to claim 7, wherein the guide tracks (34) are arranged on both sides of the leaf springs (32) running along the legs (30a, 30b) of the U-shaped holder 30.

10. The surgical instrument according to claim 1, wherein the stop (40) is arranged perpendicular to the plane of the U-shaped holder (30).

11. The surgical instrument according to claim 1, wherein the stop (40) of the gripping element (20) protrudes on both sides of the gripping element (20).

12. The surgical instrument according to claim 1, wherein a thread (24) engages in stop (40) and it runs along the lengthwise axis of the gripping element (20) and can be adjusted with the aid of a screwing element (26).

13. The surgical instrument according to claim 1, wherein the U-shaped holder (30) further comprises two holding elements (50, 52), which are joined through a parallel guide (60) and can be spread apart or closed.

14. The surgical instrument according to claim 13, wherein the two holding elements (50, 52) of the U-shaped holder (30) each have a guide track (34) on their side facing away from each other on the inside of the legs (30a, 30b) for holding the prosthesis plates (14, 16).

15. The surgical instrument according to claim 1, wherein the vertebrae stop (40) encircles the gripping element (20).

16. The surgical instrument according to claim 1, whereby the intervertebral prosthesis (10) with at least one of its components can be detachably inserted in the U-shaped holder (30) in a fixed manner.

17. The surgical instrument according to claim 16, wherein the U-shaped holder (30) further comprises an upper holding element (50) and a lower holding element (52) that spread apart with the upper holding element (50) moving in an upward direction and the lower holding element (52) moving in a lower direction.

18. The surgical instrument according to claim 17, wherein the vertebrae stop (40) extends above the upper portion of the gripping element (20) a distance that is greater than the distance through which the upper holding element (50) moves in the upward direction.

19. The surgical instrument according to claim 17, wherein the vertebrae stop (40) extends below the lower portion of the gripping element (20) a distance that is greater than the distance through which the lower holding element (50) moves in the lower direction.

20. A surgical instrument for introduction of an intervertebral prosthesis (10), having at least two prosthesis plates (14, 16) and a prosthesis core (12), comprising:
 a gripping element (20) having a lengthwise axis, a top portion and a bottom portion;

a U-shaped intervertebral prosthesis (10) holder (30), the U-shaped intervertebral prosthesis (10) holder (30) located at the distal end of the gripping element (20), and a vertebrae stop (40) movably coupled to the gripping element (20), movable along the lengthwise axis of the gripping element (20);

wherein the vertebrae stop (40) extends from beyond the top portion of the gripping element (20) to beyond the bottom portion of the gripping element (20).

* * * * *